(12) United States Patent
Chebator et al.

(10) Patent No.: US 8,496,643 B2
(45) Date of Patent: Jul. 30, 2013

(54) CAP ASSEMBLY FOR USE WITH A PREFILLED LOCK SOLUTION SYRINGE

(75) Inventors: Casey Chebator, Weymouth, MA (US); Todd Chelak, Westborough, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/334,471

(22) Filed: Dec. 22, 2011

(65) Prior Publication Data
US 2012/0095407 A1    Apr. 19, 2012

Related U.S. Application Data

(63) Continuation of application No. 12/338,358, filed on Dec. 18, 2008, now Pat. No. 8,100,885.

(60) Provisional application No. 61/008,482, filed on Dec. 20, 2007.

(51) Int. Cl.
A61M 25/16    (2006.01)
A61M 25/18    (2006.01)

(52) U.S. Cl.
USPC .......................................................... 604/533

(58) Field of Classification Search
USPC ............... 604/167.02, 167.05, 248, 533, 537, 604/192
See application file for complete search history.

(56) References Cited

U.S. PATENT DOCUMENTS

| | | | |
|---|---|---|---|
| 4,143,853 A | 3/1979 | Abramson | |
| 4,424,833 A | 1/1984 | Spector et al. | |
| 4,874,377 A | 10/1989 | Newgard et al. | |
| 4,895,346 A | 1/1990 | Steigerwald | |
| 4,909,798 A | 3/1990 | Fleischhacker et al. | |
| 4,917,668 A | 4/1990 | Haindl | |
| 4,960,412 A | 10/1990 | Fink | |
| 5,085,645 A | 2/1992 | Purdy et al. | |
| 5,135,512 A | 8/1992 | Mazurik et al. | |
| 5,215,538 A | 6/1993 | Larkin | |
| 5,242,393 A | 9/1993 | Brimhall et al. | |
| 5,308,306 A | 5/1994 | Wang | |

(Continued)

FOREIGN PATENT DOCUMENTS

| | | |
|---|---|---|
| EP | 0 325 049 | 7/1989 |
| WO | WO99/58186 | 11/1999 |

(Continued)

OTHER PUBLICATIONS

European Patent Search Report dated Oct. 18, 2011 for European Patent Appln. No. EP 11 00 7214.

(Continued)

*Primary Examiner* — Kevin C Sirmons
*Assistant Examiner* — Bradley Osinski
(74) *Attorney, Agent, or Firm* — Lisa E. Winsor, Esq.

(57) ABSTRACT

A cap assembly is disclosed for use with a lock solution delivery device. The cap assembly includes a housing defining a receptacle and having an inlet end and an outlet end. A plunger is movable axially within the receptacle from a retracted position to an advanced position and is rotatably supported within the receptacle from a first position to a second position. The plunger includes an axial extension configured to non-rotatably engage a syringe connected to the inlet end of the housing. The plunger is positioned to move from the first position to the second position in response to rotatable detachment of a syringe from the inlet end of the housing.

16 Claims, 3 Drawing Sheets

U.S. PATENT DOCUMENTS

| | | |
|---|---|---|
| 5,322,518 A | 6/1994 | Schneider et al. |
| 5,390,898 A | 2/1995 | Smedley et al. |
| 5,439,451 A * | 8/1995 | Collinson et al. ............ 604/247 |
| 5,470,319 A | 11/1995 | Mayer |
| 5,535,771 A | 7/1996 | Purdy et al. |
| 5,535,785 A | 7/1996 | Werge et al. |
| 5,549,651 A | 8/1996 | Lynn |
| 5,555,908 A | 9/1996 | Edwards et al. |
| 5,573,516 A | 11/1996 | Tyner |
| 5,676,346 A | 10/1997 | Leinsing |
| 5,738,144 A | 4/1998 | Rogers |
| 5,749,861 A | 5/1998 | Guala et al. |
| 5,776,113 A | 7/1998 | Daugherty et al. |
| 5,788,215 A | 8/1998 | Ryan |
| 5,806,551 A | 9/1998 | Meloul et al. |
| 5,806,831 A | 9/1998 | Paradis |
| 5,817,069 A | 10/1998 | Arnett |
| 5,954,313 A | 9/1999 | Ryan |
| 5,954,698 A | 9/1999 | Pike |
| 5,967,490 A | 10/1999 | Pike |
| 6,068,011 A | 5/2000 | Paradis |
| 6,068,617 A | 5/2000 | Richmond |
| 6,152,900 A | 11/2000 | Mayer |
| 6,158,458 A | 12/2000 | Ryan |
| 6,171,287 B1 | 1/2001 | Lynn et al. |
| 6,228,060 B1 | 5/2001 | Howell |
| RE37,357 E | 9/2001 | Lynn |
| 6,482,188 B1 | 11/2002 | Rogers et al. |
| 6,485,473 B1 | 11/2002 | Lynn |
| 6,572,592 B1 | 6/2003 | Lopez |
| 6,699,221 B2 | 3/2004 | Vaillancourt |
| 6,740,063 B2 | 5/2004 | Lynn |
| 6,802,490 B2 | 10/2004 | Leinsing et al. |
| 6,932,795 B2 | 8/2005 | Lopez et al. |
| RE39,334 E | 10/2006 | Lynn |
| 2002/0062106 A1 | 5/2002 | Chu et al. |
| 2005/0010176 A1 | 1/2005 | Dikeman et al. |
| 2005/0154353 A1 | 7/2005 | Alheidt |
| 2006/0247582 A1 | 11/2006 | Alheidt et al. |
| 2007/0083157 A1 | 4/2007 | Belley et al. |
| 2007/0093755 A1 | 4/2007 | Koos et al. |

FOREIGN PATENT DOCUMENTS

| | | |
|---|---|---|
| WO | WO 03/051434 | 6/2003 |
| WO | WO 2006/136769 | 12/2006 |
| WO | WO2007/025326 | 3/2007 |

OTHER PUBLICATIONS

International Search Report for European Application No. 08171488.3 dated Mar. 27, 2009.

* cited by examiner

CAP ASSEMBLY FOR USE WITH A PREFILLED LOCK SOLUTION SYRINGE

CROSS-REFERENCE TO RELATED APPLICATIONS

The present application is a continuation of U.S. application Ser. No. 12/338,358, now U.S. Pat. No. 8,100,885, filed on Dec. 18, 2008. The present application also claims the benefit of and priority to U.S. Provisional Patent Application No. 61/008,482, filed on Dec. 20, 2007, which is incorporated herein by reference in its entirety.

BACKGROUND

1. Technical Field

The present disclosure relates to lock solution delivery devices for use with indwelling catheter assemblies and, more particularly, to a cap assembly for use with a prefilled lock solution syringe for delivering a lock solution to an indwelling catheter assembly.

2. Description of Related Art

Indwelling catheter assemblies are commonly used to deliver medication to patients who require treatment over an extended period of time. Typically, an indwelling catheter assembly is inserted into a patient's vasculature and is secured to the body, e.g., the arm, of the patient. When a medication is required to be given to the patient, a syringe is secured to the catheter assembly via a reusable connector/valve, and medication is injected into the patient from the syringe through the valve/connector and through the catheter assembly.

Typically, the valve/connector includes a valve member which is pressed forwardly by the syringe during attachment of the syringe to the valve/connector, to open the valve/connector and facilitate delivery of the medication into the catheter assembly. When the syringe is removed from the valve/connector, the valve member returns to its sealed position. As the valve member returns to its sealed position, a vacuum may be drawn within the catheter assembly creating retrograde blood flow into the catheter assembly from the patient.

Syringes for delivering lock and/or flush solutions to catheter assemblies are well known. Generally, a syringe having a lock and/or flush solution is attached to the valve/connector and catheter assembly after medication has been injected into the patient. By injecting a lock and/or flush solution through the catheter assembly after a medication injection, any medication remaining in the catheter is flushed from the catheter and delivered to the patient and any blood drawn into the catheter assembly after removal of the medicament syringe is also flushed from the catheter assembly. However, upon removal of the lock solution syringe from the catheter assembly, the valve member of the valve/connector again returns to its sealed position and blood may be once again drawn into the catheter assembly. When blood is drawn into the catheter assembly, if the blood stagnates, the blood will eventually clot and occlude the catheter assembly. Further, stagnant blood provides a food source for planktonic bacteria which may lead to bio-film formation and a catheter-related bloodstream infection.

There are various types of valves/connectors that are designed to impart a positive displacement of fluid into the catheter assembly upon removal of the lock solution syringe. However, at times, an effective amount of positive displacement fluid to eliminate the existence of retrograde blood flow into the catheter assembly is not achievable. This may be partially due to the limited amount of fluid capable of being displaced by known valves/connectors which may be less than 1 mL. Furthermore, these valves/connectors are reusable and have been susceptible to bacterial contamination.

Accordingly, a need exists in the medical arts for an improved device for effectively flushing and locking a catheter assembly after injection of a medication into the catheter assembly which can be removed from the catheter assembly without drawing blood into the catheter assembly.

SUMMARY

A cap assembly is disclosed for use with a lock solution delivery device which includes a housing defining a receptacle and having an inlet end and an outlet end. The inlet end defines an opening and is adapted to releasably and rotatably engage a syringe. The outlet end defines an outlet conduit and is adapted to releasably engage an indwelling catheter assembly. A plunger is axially movably positioned within the receptacle from a retracted position to an advanced position and is rotatably supported within the receptacle from a first position to a second position. The plunger includes an axial extension configured to non-rotatably engage a syringe connected to the inlet end of the housing. The plunger assembly includes at least one protrusion and the housing includes at least one slot dimensioned to slidably receive the at least one protrusion. The at least one protrusion is misaligned with the at least one slot when the plunger is in the first position to retain the plunger in the retracted position and the at least one protrusion is aligned with the at least one slot when the plunger is in the second position to facilitate movement of the plunger from the retracted position to the advanced position. In one embodiment, a biasing member is positioned within the receptacle to urge the plunger towards the advanced position. The biasing member may include a coil spring. In one embodiment, the plunger is positioned to move from the first position to the second position in response to rotatable detachment of a syringe from the inlet end of the housing. The distal end of the plunger may have a cylindrical portion which is movably received within a cylindrical portion of the receptacle. The cylindrical portion of the plunger includes at least one annular sealing rib positioned to slidable and sealingly engage an inner wall of the cylindrical portion of the receptacle.

The at least one slot may include a plurality of longitudinal slots formed in a stepped portion of the housing. Each slot is dimensioned to slidably receive one of the at least one protrusions. A proximal surface of the stepped portion defines a shoulder, wherein the at least one protrusion rests on the shoulder when the plunger is in the first position. In one embodiment, the at least one protrusion includes a plurality of radially extending fingers formed on the plunger. Each of the radially extending fingers is aligned with a respective one of the plurality of longitudinal slots when the plunger is in the second position.

In one embodiment, the axial extension defines a fluid channel. A resilient valve member may be formed on the axial extension adjacent an outlet end of the fluid channel of the axial extension to prevent fluid from entering the cap assembly during shipping and/or transportation of the cap assembly.

BRIEF DESCRIPTION OF THE DRAWINGS

Various embodiments of the presently disclosed cap assembly for use with a prefilled lock solution syringe are disclosed herein with reference to the drawings wherein.

DETAILED DESCRIPTION OF EMBODIMENTS

Figure 1:
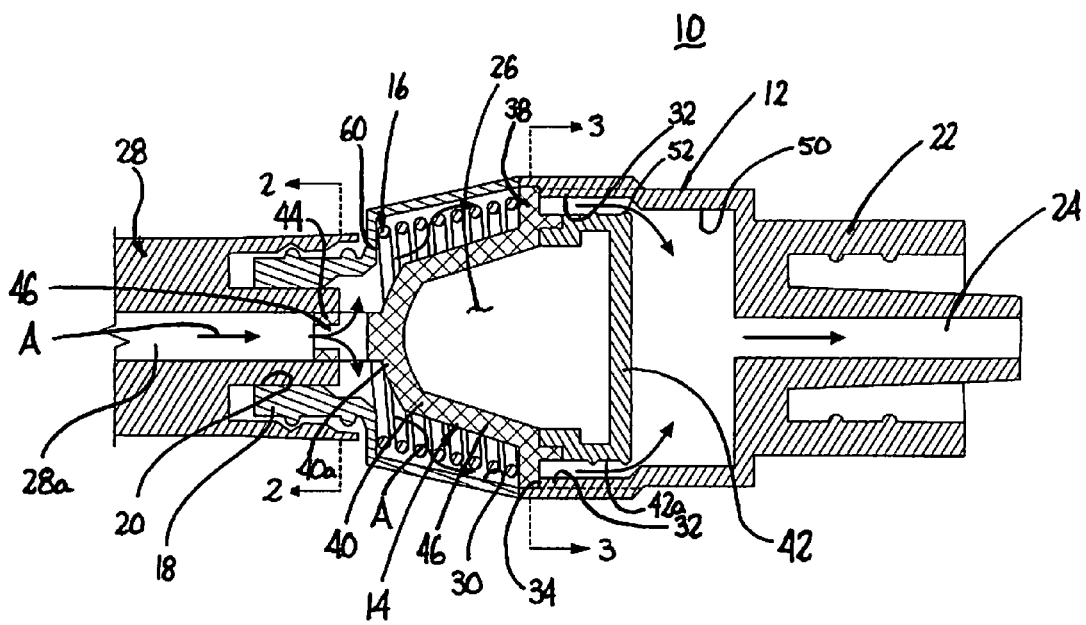
FIG. 1 is a side cross-sectional view of one embodiment of the presently disclosed cap assembly, with the plunger in a retracted position, shown connected to the distal end of a fluid delivery device.

Embodiments of the presently disclosed cap assembly for use with a prefilled lock solution syringe will now be described in detail with reference to the drawings wherein like reference numerals designate identical or corresponding elements in each of the several views. In this description, the term proximally is generally used to indicate the relative nearness of a referenced item to a clinician using the assembly and the term distal is used to indicate the remoteness of a referenced item to a clinician using the device.

Referring to FIG. 1, cap assembly 10 includes a housing 12, a plunger assembly 14 and a biasing member 16. Housing 12 includes an inlet connector 18 defining an inlet opening 20, an outlet connector 22, and an outlet conduit 24. Housing 12 also defines a receptacle 26 for movably receiving plunger assembly 14 as will be discussed in further detail below. Inlet connector 18 includes a female luer-type connector which is configured to engage the distal end of a fluid delivery device 28, e.g., a syringe. Outlet connector 22 includes a male luer-type connector which is configured to releasably engage an indwelling catheter assembly (not shown).

Figure 3:
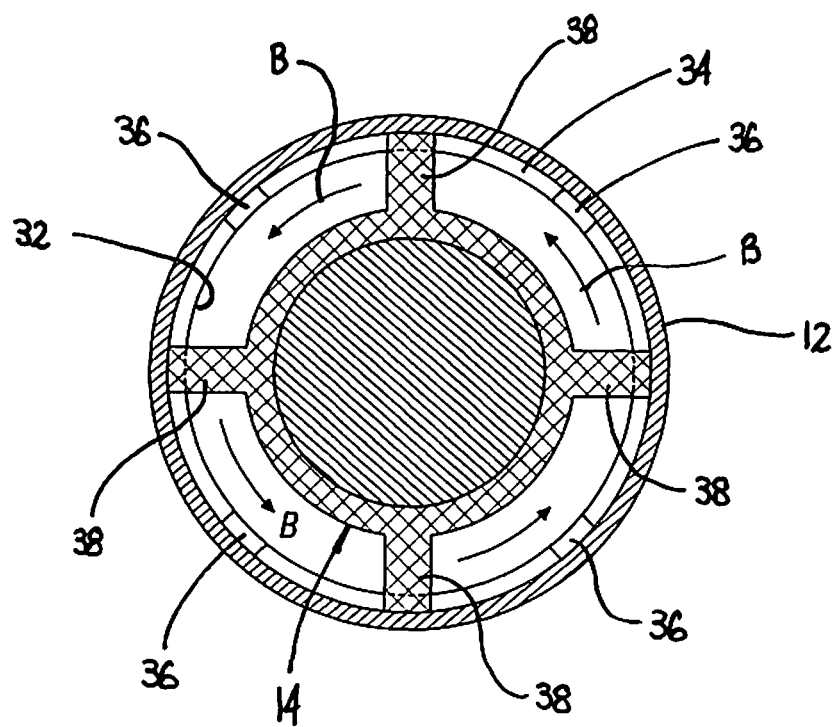
FIG. 3 is a cross-sectional view of the cap assembly shown in FIG. 1 taken along section lines 3-3 of FIG. 1.

Referring also to FIG. 1, housing 12 includes an inner wall 30 which defines receptacle 26. A central portion of inner wall 30 defines a stepped portion 32. Stepped portion 32 defines an annular shoulder 34 (FIG. 3) and a plurality of spaced longitudinal slots 36 (FIG. 3). Spaced longitudinal slots 36 are dimensioned to slidably receive radially extending fingers or tabs 38 as will be discussed in further detail below. Although four slots 36 and tabs 38 are shown (FIG. 3), one or more slots 36 and tabs 38 may be provided.

Plunger assembly 14 includes a plunger body 40 and a plunger head 42 which are secured together using known fastening techniques, e.g., adhesives, welding interlocking structure, etc., to define an integral assembly 14. It is also envisioned that plunger assembly 14 may be of unitary construction. Plunger body 40 has a proximal end 40a defining an axial extension 44 and a bell-shaped body portion 46. Radial fingers or tabs 38 extend radially from a distal end of body 40 and are positioned to rest on shoulder 34 of housing 12 (FIG. 3) when plunger assembly 14 is in a retracted position. Radial fingers 38 are also dimensioned to be slidably received in longitudinal slots 36 formed along inner housing wall 30 of housing 12. Axial extension 44 of plunger body 40 is dimensioned to extend into a delivery channel 28a of delivery device 28 (FIG. 1) and defines a T-shaped channel 46. Channel 46 allows fluid to flow from delivery device 28 into receptacle 26 of housing 12 when axial extension 44 is positioned in delivery channel 28a of delivery device 28. It is envisioned that channel 46 may have other configurations such as Y-shaped, F-shaped, or any other configuration that allows fluid to flow from delivery device 28 into receptacle 26. As illustrated in FIG. 3, axial extension 44 has a non-circular outer geometry which is illustrated as being substantially triangular, although other non-circular configurations are envisioned, e.g., square, rectangular, trapezoidal, etc. The outer geometry of axial extension 44 should be such that when axial extension 44 of plunger assembly 14 is received in delivery channel 28a of delivery device 28, delivery device 28 and plunger assembly 14 are rotatably fixed together.

Figure 4:
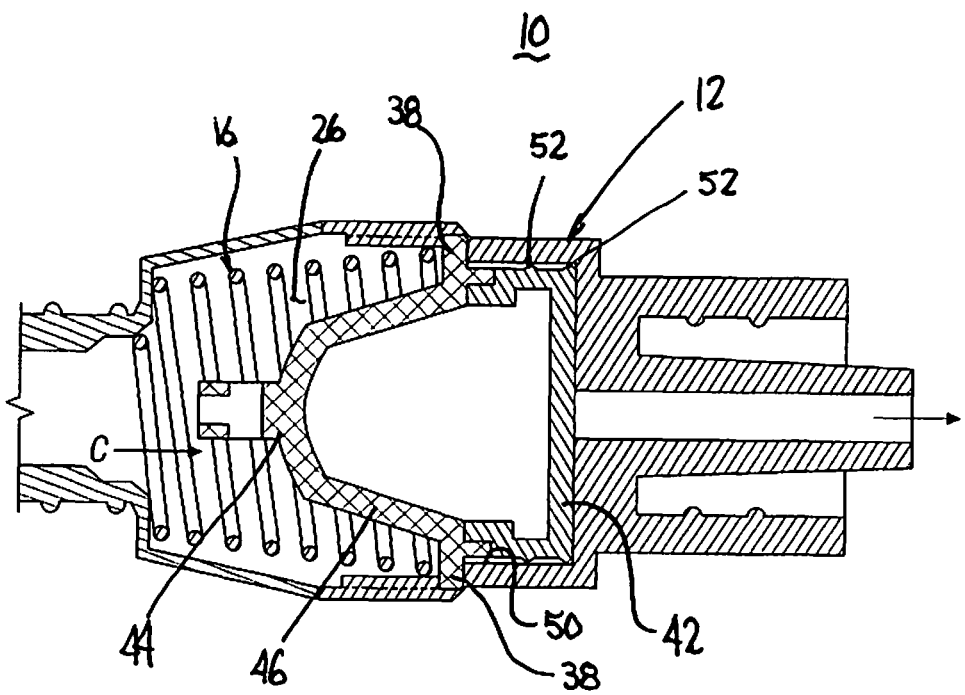
FIG. 4 is a side cross-sectional view of the cap assembly shown in FIG. 1 with the plunger in an advanced position.

Plunger head 42 is substantially cylindrical and is dimensioned to be slidably received within a cylindrical portion 50 of housing 12. An outer wall 42a of plunger head 42 includes one or more annular sealing ribs 52 which are positioned to sealingly engage an inner wall of cylindrical portion 50 of housing 12 as plunger assembly 14 moves from its retracted position (FIG. 1) to its advanced position (FIG. 4). Movement of plunger head 42 through cylindrical portion 50 of housing 12 forces fluid located within cylindrical portion 50 through outlet conduit 24 into an indwelling catheter assembly (not shown).

Biasing member 16 which is shown as a coil spring is positioned within receptacle 26 between a proximal shoulder 60 of housing 12 and radial fingers 38. Biasing member 16 urges plunger assembly 14 distally within receptacle 26 such that when radial fingers 38 are misaligned with longitudinal slots 36, radial fingers 38 rest on shoulders 34 of stepped portion 32 of housing 12, and when radial fingers 38 are aligned with longitudinal slots 36, biasing member 16 urges plunger assembly 14 from its retracted position (FIG. 1) to its advanced position (FIG. 4).

Figure 2:
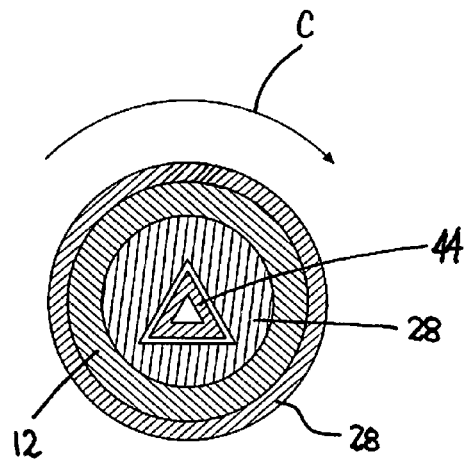
FIG. 2 is a cross-sectional view taken along section lines 2-2 of FIG. 1.

In use, cap assembly 10 is attached to a syringe 28 including a locking solution. It is envisioned that cap assembly 10 and syringe 28 may be preassembled. It is also envisioned that cap assembly 10 may be prefilled with a locking solution and further include a means for selectively closing the distal end of outlet conduit 24 and/or the proximal end of inlet connector 18 such as by attaching a removable luer cap. When cap assembly 10 is secured to syringe 28, axial extension 44 is received within delivery channel 28a of syringe 28. As discussed above, axial extension 44 and delivery channel 28a have non-circular configurations to rotatably fix axial extension 44 to syringe 28 (FIG. 2). In this condition, radial fingers 38 are misaligned with longitudinal slots 36 such that radial fingers 38 are seated on shoulders 34 (FIG. 3) and plunger assembly 14 is retained in its retracted position (FIG. 1). Distal connector 22 can be connected to an indwelling catheter assembly (not shown) and fluid can be injected from syringe 28, through cap assembly 10 into the indwelling catheter assembly (not shown) along the path indicated by arrows "A" in FIG. 1. When this occurs, locking fluid will fill cap assembly 10 and flow into the indwelling catheter assembly to force medicament and/or blood positioned within the catheter assembly into the patient. Additionally, fluid can be aspirated from the indwelling catheter assembly (not shown), through cap assembly 10 into syringe 28 in the reverse direction of path "A". When syringe is subsequently separated from cap assembly 10 by rotating syringe 28 in relation to cap assembly 10 in the direction indicated by arrow "C" (FIG. 2), axial extension 44, which is rotatably fixed to syringe 28, will rotate to rotate plunger assembly 14 within receptacle 26. When plunger assembly 14 rotates, radial fingers 38 are rotated over shoulders 34 in the direction indicated by arrows "B" in FIG. 3 into alignment with longitudinal slots 36. When radial fingers 38 move into alignment with longitudinal slots 36, biasing member 16 moves plunger assembly 14 to its advanced position (FIG. 4) to force fluid from cylindrical portion 50 of housing 12 through outlet conduit 24 into the indwelling catheter assembly (not shown). As such, blood is not withdrawn into the indwelling catheter assembly when syringe 28 is separated from housing 12 of cap assembly 10. Furthermore, plunger assembly 14 is also capable of displacing large amounts of fluid, for example 1-2 mL or more, from cylindrical portion 50 of housing 12 into the indwelling catheter assembly (not shown). Cap assembly 10 remains attached to the indwelling catheter until it is desired to inject a medicament into the catheter assembly or withdraw blood from a patient. Then, it can be removed from the catheter assembly and the flushing/locking process described above can be repeated after medicament administration or blood withdrawal.

Figure 5:
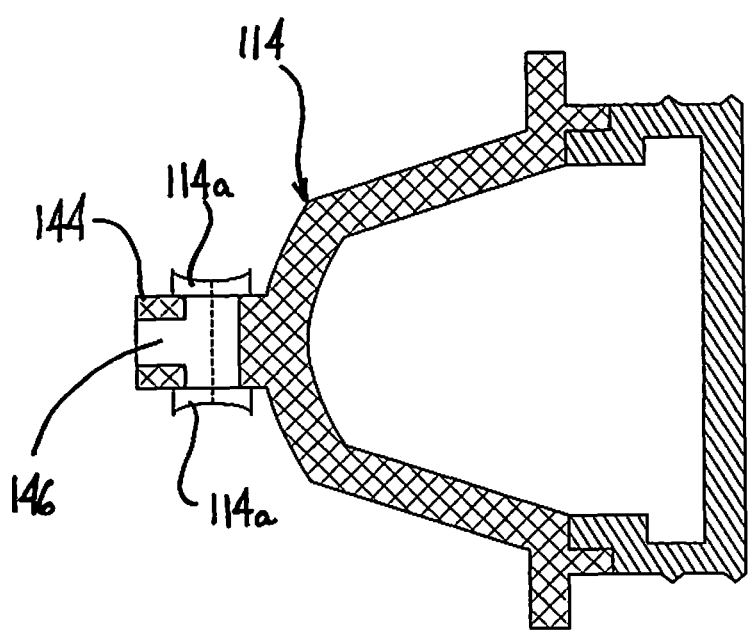
FIG. 5 is a side cross-sectional view of an alternative embodiment of the plunger of the presently disclosed cap assembly.

FIG. 5 illustrates an alternate embodiment of the presently disclosed plunger assembly shown generally as 114. Plunger assembly 114 is substantially similar to plunger assembly 14 except that plunger assembly 114 further includes a resilient valve or sealing element 114a formed at the outlet end of T-shaped channel 146. Resilient valve 114a may be in the form of a slit-type valve. Resilient valve 114a remains closed until a predetermined positive or negative pressure is created in channel 146, such as by actuating syringe 28 (FIG. 1). When the predetermined positive pressure is reached in channel 146, resilient valve 114a flexes outwardly to allow fluid to flow from channel 146 into the housing receptacle (see FIG. 1). When the predetermined negative pressure is reached in channel 146, resilient valve 114a flexes inwardly to allow fluid flow from the housing receptacle into channel 146. Furthermore, a proximal end of resilient valve 114a may be in contact with the distal end of syringe 28 to prevent fluid from flowing through the gap that may exist between the outside surface of axial extension 144 and the wall of delivery channel 28a. Plunger assembly 114 prevents lock solution from entering the receptacle of the cap assembly during transportation and storage of the syringe and cap assembly when the two parts are preassembled. A removable cover (not shown) may be provided to seal outlet conduit 24 to guard or prevent contaminants from entering the cap assembly prior to use.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A cap assembly comprising:
    a housing defining a receptacle and including an inlet opening and an outlet opening;
    a plunger movably positioned within the receptacle from a first position to a second position and to a third position, the plunger defining a fluid flow path between the inlet opening and the outlet opening when the plunger is in the first position and obstructing fluid flow between the inlet opening and the outlet opening when the plunger is in the third position, the plunger being positioned and configured to engage a syringe through the inlet opening; and
    a biasing member positioned to urge the plunger towards the third position;
    wherein the plunger is configured to force fluid from the receptacle through the fluid outlet when the plunger moves from the second position to the third position.

2. The cap assembly according to claim 1, wherein the housing and the plunger include engaging structure to prevent movement of the plunger towards the third position when the plunger is in the first position.

3. The cap assembly according to claim 2, wherein the engaging structure includes at least one protrusion formed on the plunger and an annular shoulder formed on the housing.

4. A cap assembly comprising:
    a housing defining a receptacle and including an inlet opening and an outlet opening;
    a plunger movably positioned within the receptacle from a first position to a second position and to a third position, the plunger defining a fluid flow path between the inlet opening and the outlet opening when the plunger is in the first position and obstructing fluid flow between the inlet opening and the outlet opening when the plunger is in the third position, the plunger being positioned and configured to engage a syringe through the inlet opening; and
    a biasing member positioned to urge the plunger towards the third position;
    wherein the plunger is configured to force fluid from the receptacle through the fluid outlet when the plunger moves from the second position to the third position, the housing and the plunger including engaging structure to prevent movement of the plunger towards the third position when the plunger is in the first position, the engaging structure including at least one protrusion formed on the plunger and an annular shoulder formed on the housing;
    wherein the annular shoulder defines at least one slot which is dimensioned to receive the at least one protrusion to facilitate movement of the plunger towards the third position, the at least one protrusion and the at least one slot being misaligned when the plunger is in the first position and aligned when the plunger is in the second position.

5. The cap assembly according to claim 4, wherein the plunger is rotatably movable between the first and second positions and axially movable between the second and third positions.

6. The cap assembly according to claim 5, wherein an inlet end of the housing defining the inlet opening is adapted to releasably engage a syringe and an outlet end of the housing defining the outlet opening is adapted to releasably engage an indwelling catheter assembly.

7. The cap assembly according to claim 6, wherein the plunger includes an axial extension which is configured to non-rotatably engage a distal end of a syringe such that when the syringe is disengaged from the inlet end of the housing, the plunger is moved from the first position to the second position.

8. The cap assembly according to claim 7, wherein the axial extension defines a fluid channel.

9. The cap assembly according to claim 8, further including a resilient valve member formed on the axial extension adjacent an outlet end of the fluid channel of the axial extension.

10. The cap assembly according to claim 4, wherein the at least one protrusion includes a plurality of radially extending fingers formed on the plunger, each of the radially extending fingers being aligned with a respective one of the at least one slot when the plunger is in the second position.

11. The cap assembly according to claim 1, wherein the plunger is rotatably movable between the first and second positions and axially movable between the second and third positions.

12. The cap assembly according to claim 11, wherein an inlet end of the housing defining the inlet opening is adapted to releasably engage a syringe and an outlet end of the housing defining the outlet opening is adapted to releasably engage an indwelling catheter assembly.

13. The cap assembly according to claim 12, wherein the plunger includes an axial extension which is configured to engage a distal end of a syringe such that when the syringe is disengaged from the inlet end of the housing, the plunger is moved from the first position to the second position.

14. A cap assembly according to claim 11, wherein the plunger is adapted to be movable from the first position to the second position in response to disengagement of a syringe from the housing.

15. The cap assembly according to claim 1, wherein the biasing member is a coil spring.

16. The cap assembly according to claim 1, wherein the plunger is rotatably positioned within the housing and is adapted to rotate between the first position and the second position.

* * * * *